US009468640B2

(12) United States Patent
De Bruyn et al.

(10) Patent No.: US 9,468,640 B2
(45) Date of Patent: *Oct. 18, 2016

(54) PIPERIDIN-4-YL-PYRIDAZIN-3-YLAMINE DERIVATIVES AS FAST DISSOCIATING DOPAMINE 2 RECEPTOR ANTAGONISTS

(71) Applicant: Janssen Pharmaceutica N.V., Beerse (BE)

(72) Inventors: Marcel Frans Leopold De Bruyn, Beerse (BE); Gregor James Macdonald, Beerse (BE); Ludo Edmond Josephine Kennis, Lier (BE); Xavier Jean Michel Langlois, Beerse (BE); Frans Alfons Maria Van den Keybus, Beerse (BE); Yves Emiel Maria Van Roosbroeck, Beerse (BE)

(73) Assignee: JANSSEN PHARMACEUTICA NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,873

(22) Filed: Jan. 26, 2015

(65) Prior Publication Data

US 2015/0141432 A1 May 21, 2015

Related U.S. Application Data

(63) Continuation of application No. 12/091,219, filed as application No. PCT/EP2006/067696 on Oct. 24, 2006, now Pat. No. 8,940,743.

(30) Foreign Application Priority Data

Oct. 26, 2005  (EP) .................................... 05110028
Jan. 10, 2006  (EP) .................................... 06100209
Feb. 10, 2006  (EP) .................................... 06101545

(51) Int. Cl.
C07D 401/12 (2006.01)
C07D 409/14 (2006.01)
A61K 31/501 (2006.01)

(52) U.S. Cl.
CPC ........... A61K 31/501 (2013.01); C07D 401/12 (2013.01); C07D 409/14 (2013.01)

(58) Field of Classification Search
None
See application file for complete search history.

(56) References Cited

U.S. PATENT DOCUMENTS

| 3,933,823 A | 1/1976 | Denzel et al. |
| 3,933,832 A | 1/1976 | Langbein et al. |
| 4,126,689 A | 11/1978 | Sanczuk et al. |
| 4,197,304 A | 4/1980 | Hermans et al. |
| 4,585,471 A | 4/1986 | Forster et al. |
| 5,461,053 A | 10/1995 | Boigegrain et al. |
| 5,560,931 A | 10/1996 | Eickhoff et al. |
| 5,736,545 A | 4/1998 | Gadwood et al. |
| 5,866,589 A | 2/1999 | Romero et al. |
| 5,958,923 A | 9/1999 | Hellendahl et al. |
| 7,335,658 B2 | 2/2008 | Chakka et al. |
| 7,754,774 B2 | 7/2010 | Kobayashi et al. |
| 8,058,243 B2 | 11/2011 | Tyers et al. |
| 8,940,743 B2* | 1/2015 | De Bruyn ............ C07D 401/12 514/252.03 |
| 2003/0236259 A1 | 12/2003 | Hohlweg et al. |
| 2007/0081953 A1 | 4/2007 | Dahms |
| 2008/0227791 A1 | 9/2008 | DeBruyn et al. |
| 2010/0063058 A1 | 3/2010 | MacDonald et al. |
| 2010/0069394 A1 | 3/2010 | MacDonald et al. |
| 2010/0076187 A1 | 3/2010 | MacDonald et al. |
| 2010/0092505 A1 | 4/2010 | Bianchi et al. |
| 2010/0120860 A1 | 5/2010 | MacDonald et al. |
| 2010/0137368 A1 | 6/2010 | MacDonald et al. |
| 2010/0210687 A1 | 8/2010 | Cooper et al. |
| 2011/0112107 A1 | 5/2011 | Bartolomé-Nebreda |
| 2011/0130408 A1 | 6/2011 | Bartolm -Nebreda et al. |

FOREIGN PATENT DOCUMENTS

| CA | 2009501 | 8/1990 |
| DE | 2642856 | 3/1977 |
| DE | 3218482 | 11/1983 |
| EP | 211457 | 2/1987 |
| EP | 281309 | 9/1988 |
| EP | 532178 | 3/1993 |
| EP | 1443046 | 8/2004 |
| EP | 1621538 | 2/2006 |
| EP | 1506185 | 5/2006 |
| GB | 1539473 | 1/1979 |
| WO | WO 95/18118 | 7/1995 |
| WO | WO 96/02249 | 2/1996 |
| WO | WO 96/18628 | 6/1996 |
| WO | WO 96/35666 | 11/1996 |
| WO | WO 97/43279 | 11/1997 |
| WO | WO 99/09025 | 2/1999 |

(Continued)

OTHER PUBLICATIONS

International Search Report re: PCT/EP2006/067696 dated Mar. 13, 2007.
Abbott, A., Nature, vol. 447, May 24, 2007, p. 368-370.
Arlt, M. et al., Bioorganic & Medicinal Chemistry Letters; vol. 8; No. 15; p. 2033-2038, 1998.
Bartoszyk et al., "Anxiolytic Effects of Dopamine Receptor Ligands: I. Involvement of Dopamine Autoreceptors" Life Sciences, Pergamon Press, Oxford, GB, vol. 62, No. 7, Jan. 1, 1998, pp. 649-663.

(Continued)

Primary Examiner — Emily Bernhardt

(57) ABSTRACT

The present invention relates to compounds that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

2 Claims, No Drawings

(56) References Cited

FOREIGN PATENT DOCUMENTS

| | | |
|---|---|---|
| WO | WO 99/36407 A1 | 7/1999 |
| WO | WO 01/98273 | 12/2001 |
| WO | WO 02/068409 | 9/2002 |
| WO | WO 03/045353 | 6/2003 |
| WO | WO 03/049736 | 6/2003 |
| WO | WO 03/062215 | 7/2003 |
| WO | WO 03/066604 | 8/2003 |
| WO | WO 03/072548 | 9/2003 |
| WO | WO 2004/058729 | 7/2004 |
| WO | WO 2004/085406 | 10/2004 |
| WO | WO 2004/098555 | 11/2004 |
| WO | WO 2005/005779 | 1/2005 |
| WO | WO 2005/009976 | 2/2005 |
| WO | WO 2005/011655 | 2/2005 |
| WO | WO 2005/046581 | 5/2005 |
| WO | WO 2005/077914 | 8/2005 |
| WO | WO 2005/090317 | 9/2005 |
| WO | WO 2005/013907 | 11/2005 |
| WO | WO 2005/105779 | 11/2005 |
| WO | WO 2005/117883 | 12/2005 |
| WO | WO 2005/123692 | 12/2005 |
| WO | WO 2005/123693 | 12/2005 |
| WO | WO 2006/034440 | 3/2006 |
| WO | WO 2006/055187 | 5/2006 |
| WO | WO 2007/001975 | 1/2007 |
| WO | WO 2007/048779 | 5/2007 |
| WO | WO 2007/130383 | 11/2007 |
| WO | WO 2008/019967 | 2/2008 |
| WO | WO 2008/068507 | 6/2008 |
| WO | WO 2008/098892 | 8/2008 |
| WO | WO 2010/012758 | 2/2010 |

OTHER PUBLICATIONS

Benjamin, et al., Biochemical Pharmacology; vol. 72; No. 6; p. 770-782, 2006.
Bianchi "Current Issues in CNS drug" p. 1-3 (2011).
Binggeli et al., CA148:285064 (2008).
Braga et al., Roy. Soc. Chem. Chem. Commun. p. 3635-3645 (2005).
Cell Surface Receptor, Wikipedia, p. 1-6 (2012).
Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).
Contreras, Jean Marie, "Aminopyridazines as Acetylcholinesterase Inhibitors", J. Med. Chem. (1999),42 (4), 730-741.
Cook et al., CA132__347492 (2000).
Dean et al., J. Org. Chem. 1993, 58, 7916-7917.
Eichenberger, K.; Rometsch, R..; Druey, J. Australian Journal of Chemistry 1956, 9, 1755-1764. See English abstract provided.
Fryatt et al., J. Bioorganic and Medicinal Chemistry, 2004, 12, 1667-1687.
Garzya et al., Bioorganic & Medicinal Chemistry Letters, 17 (2007) 400-405.
Genin et al., "Synthesis and structure-activity relationships of the (alkylamino)piperidine-containing BHAP class of non-nucleoside reverse transcriptase inhibitors: effect of 3-alkylpyridine ring substitution" J. Med. Chem., vol. 42, No. 20, 1999, pp. 4140-4149.
Genin et al., "Synthesis and bioactivity of novel bis(heteroaryl)piperazine (BHAP) reverse transcriptase inhibitors: structure-activity relationships and increased metabolic stabilita of novel substituted pyri di ne' analogs" J. Med. Chem., vol. 39, No. 26, 1996, pp. 5267-5275.
Gillaspy et al., Tetrahedron Letters 1995, 36, 7399-7402.
Goodman et al., Tetrahedron 1999, 55, 15067-15070.
Goodman and Gilman's The Pharmacologic Basis of Therapeutics, 12th Edition, Chapter 16, "Pharmacotherapy of Psychosis and Mania" by Jonathan M. Meyer, pp. 417-455, 2011.
Griesser, in Chapter 8, The Importance of Solvates (pp. 211-230), In the text, Polymorphism: In the Pharmaceutical Industry, Hilfiker, 2006.
Grundt et al., Bioorg. Med. Chem. Lett 17(3) 745-749 (2007).
Holenz et al., Drug discovery today; vol. 11; No. 7-8; p. 283-299, 2006.
Joyce et al., (2005) Dopamine D3 receptor antagonist as therapeutic agents. Drug Discovery Today 10: 917-925.
Kapitulnik, J., Frontiers in Pharm. p. 1-2, (2011).
Kapur, et al. , "Does fast dissociation from the dopamine D2 receptor explain the action of atypical antipsychotics? A new hypothesis", Am. J. Psychiatry, 2001,158:3, p. 360-369.
Kikuchi et al., J. Med. Chem. (1999), 42 (4), 730-741.
Kortagere et al., "Certain 1,4-disubstituted aromati c piperidines and piperazines with extreme selectivity for the Dopamine D4 receptor interact with a common receptor microdomain" Molecular Pharmacology, vol. 66, No. 6, 2004, pp. 1491-1499.
Kula et al., "Neuropharmacological assessment of potential dopamine D4 receptor-selective radioligands" European Journal of Pharmacology, Amsterdam, NL, vol. 367, Jan. 1, 1999, pp. 139-142.
Kula et al., "RBI-257: A highly potent dopamine D receptor-selective ligand", European Journal of Pharmacology, 331 (1997), pp. 333-336.
Kula et al., CA127:171455 (1997), Abstract version.
Leysen, J., et al.,"The dissociation rate of unlabeled dopamine antagonists and agonists from the dopamine-D2 receptor, application of an original filter method", Journal of Receptor Research, 1984, 4(7), 817-845.
Liu et al., Drug Development Research, 70: 145-168 (2009).
Lovenberg et al., Cloning of rat histamine H3 receptor reveals distinct species pharmacological profiles. J Pharmacol Expt Ther 2000;293:771-778.
Mitchell et al., Pharmacology & Therapeutics 108 (2005), 320-333.
Moragues, J. et al., "Dopaminergic Activity in a series of n-substituted 2-aminopyrimidines" Farmaco, vol. 35, No. 11, 1980, pp. 951-964.
Munson et al., "Synthesis of 2-AlkYlamino-3-fluoropyridines Using Buchwald Conditions" Synthetic Communications, Taylor & Francis, Philadelphia, PA, vol. 34, No. 5, Jan. 1, 2004, pp. 759-766.
Okuyama et al., Life Sci. 65(20) 2109-2125 (1999).
Phedias et al., CA148:509885 (2008).
Poupaert, J.H., Drug Design: Basic Principles and Applications, in 2 Encyclopedia of Pharmaceutical Technology 1362-1369, 1367 (James Swarbrick ed., 3rd ed., 2007).
Rodefer et al., Neuropsychopharmacology (2008) 2657-2666; [may be noted in spec as Rodefer et al., Neuropsychopharmacology (2007), 1-10].
Schlachter et al. "Substituted 4-aminopiperidines having high in vitro affinity and selectivity for the cloned human dopami ne D4 receptor" European Journal of Pharmacology, vol. 322, 1997, pp. 283-286.
Seddon, K., Crystal. Growth & Design 4(6)1087 (2004).
Tao et al., Tetrahedron Lett. 2003, 44, 7993-7996.
TenBrink, CA124:8845 (1995).
Vippagunta et al., "Crystalline solids", Adv. Drug Delivery Reviews 48 (2001) 3-26.
Wood et al., Exp. Opin. Invest. Drugs 1696)771-775 (2007).
Xiao et al., Bioorg, Med. Chem. Lett. v.21, p. 861-864 (2011).
Yamada et al., Involvement of Septal and Striatal Dopamine D-2 Receptors in Yawning Behavior in Rats, Psychopharmacology, vol. 1, 1986, pp. 9-13.
Zablotskaya et al., Chem. Het. Compo v.38 (7), p. 859-866 (2002).
Zhang et al., Exp. Opin. Ther. Patents 16(5) 587-630 (2006).
Fisas et al., British Journal of Pharmacology. 2006, 148: 973-983.
Hannon et al., Acta Biologica Szegediensis. 2002, 46(1-2): 1-12.
Eichenberger, K.; Rometsch, R..; Druey, J. Australian Journal of Chemistry 1956, 9, 1755-1764. See English summary provided at end of article.

\* cited by examiner

PIPERIDIN-4-YL-PYRIDAZIN-3-YLAMINE DERIVATIVES AS FAST DISSOCIATING DOPAMINE 2 RECEPTOR ANTAGONISTS

CROSS REFERENCE TO RELATED APPLICATIONS

This application is a continuation of U.S. application Ser. No. 12/091,219 filed on Apr. 23, 2008, which is a national stage of PCT Application No. PCT/EP2006/067696, filed Oct. 24, 2006, which claims priority from European Patent Application No. 06101545.9, filed Feb. 10, 2006; European Patent Application No. 06100209.3, filed Jan. 10, 2006; and European Patent Application No. 05110028.7, filed Oct. 26, 2005, the entire disclosures of which are hereby incorporated in their entirety.

FIELD OF THE INVENTION

The present invention relates to compounds that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

BACKGROUND PRIOR ART

J. Med. Chem. (1999), 42 (4), 730-741 discloses 6-phenyl-N-[1-(phenylmethyl)-4-piperidinyl]-3-pyridazinamine and analogous compounds as acetylcholinesterase inhibitors.

Farmaco, Vol. 35, no. 11, 1980, pages 951-964 discloses substituted N-[4-piperidinyl]-2-aminopyrimidines having dopaminergic activity, i.e. most of the disclosed compounds are agonists at the dopamine D2 receptor. Since none of the compounds tested antagonized the stereotyped behavior induced by a subsequent dose of apomorphine they may also be considered to be devoid of dopamine receptor blocking properties. The compounds of the present invention differ in the presence of a pyridazine instead of a pyrimidine and the unexpected finding that they exert an antagonistic effect at the dopamine D2 receptor.

DESCRIPTION OF THE INVENTION

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affect, poverty of speech and the inability to experience pleasure. In addition, schizophrenic patients are suffering from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered; it proposes that hyperactivity of dopamine transmission is responsible for the positive symptoms observed in schizophrenic patients. This hypothesis is based on the observation that dopamine enhancing drugs, such as amphetamine or cocaine, may induce psychosis, and on the correlation that exists between clinical doses of antipsychotics and their potency in blocking dopamine D2 receptors. All marketed antipsychotics mediate their therapeutic efficacy against positive symptoms by blocking the dopamine D2 receptor. Apart from the clinical efficacy, it appears that the major side effects of antipsychotics, such as extrapyramidal symptoms (EPS) and tardive dyskinesia, are also related to dopamine antagonism. Those debilitating side effects appear most frequently with the typical or first generation of antipsychotic (e.g., haloperidol). They are less pronounced with the atypical or second generation of antipsychotic (e.g., risperidone, olanzapine) and even virtually absent with clozapine, which is considered the prototypical atypical antipsychotic. Among the different theories proposed for explaining the lower incidence of EPS observed with atypical antipsychotics, the one that has caught a lot of attention during the last fifteen years, is the multireceptor hypothesis. It follows from receptor binding studies showing that many atypical antipsychotics interact with various other neurotransmitter receptors in addition to dopamine D2 receptors, in particular with the serotonin 5-HT2 receptors, whereas typical antipsychotic like haloperidol bind more selectively to the D2 receptors. This theory has been challenged in recent years because all major atypical antipsychotics fully occupy the serotonin 5-HT2 receptors at clinically relevant dosages but still differ in inducing motor side-effects. As an alternative to the multireceptor hypothesis, Kapur and Seeman ("Does fast dissociation from the dopamine D2 receptor explain the action of atypical antipsychotics?: A new hypothesis", Am. J. Psychiatry 2001, 158:3 p. 360-369) have proposed that atypical antipsychotics can be distinguished from typical antipsychotics by the rates at which they dissociate from dopamine D2 receptors. The fast dissociation from the D2 receptor would make an antipsychotic more accommodating of physiological dopamine transmission, permitting an antipsychotic effect without motor side effects. This hypothesis is particularly convincing when one considers clozapine and quetiapine. These two drugs have the fastest rate of dissociation from dopamine D2 receptors and they carry the lowest risk of inducing EPS in humans. Conversely, typical antipsychotics associated with a high prevalence of EPS, are the slowest dissociating dopamine D2 receptor antagonists. Therefore, identifying new drugs based on their rate of dissociation from the D2 receptor appears as a valid strategy to provide new atypical antipsychotics. An additional goal is to combine fast dissociating properties with selectivity for dopamine D2 receptors. The multiple receptor profile of current atypical antipsychotics is thought to be the cause of other side effects, such as weight gain and diabetes. Searching for selective D2 antagonists has been ignored as an approach for some time but it is our belief that using more selective compounds in clinic may reduce the occurrence of metabolic disorders associated with current atypical antipsychotic drugs.

It is the object of the present invention to provide novel compounds that are fast dissociating dopamine D2 receptor antagonists which have an advantageous pharmacological profile as explained hereinbefore, in particular reduced motor side effects, and moderate or negligible interactions with other receptors resulting in reduced risk of developing metabolic disorders.

This goal is achieved by the present novel compounds according to Formula (I):

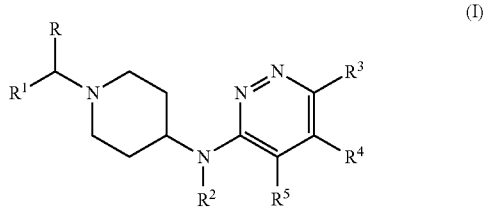

the pharmaceutically acceptable salts, hydrates and solvates thereof, and stereoisomeric forms thereof, wherein R is hydrogen or $C_{1-6}$alkyl;

$R^1$ is phenyl; phenyl substituted with 1, 2 or 3 substituents each independently selected from the group consisting of hydrogen, halo, cyano, $C_{1-4}$alkyl, $C_{1-4}$alkyloxy, perfluoro$C_{1-4}$alkyl, di$C_{1-4}$alkylamino; thienyl; thienyl substituted with 1 or 2 substituents selected from the group consisting of halo and $C_{1-4}$alkyl; $C_{3-8}$cycloalkyl; or $C_{5-7}$cycloalkenyl;

$R^2$ is hydrogen or $C_{1-6}$alkyl;

$R^3$ is halo, $C_{1-4}$alkyl or perfluoro$C_{1-4}$alkyl; and $R^4$ and $R^5$ each independently are hydrogen or halo.

The compounds according to the invention are fast dissociating $D_2$ receptor antagonists, an activity not attributed to any of the 6-phenyl-N-[4-piperidinyl]-3-pyridazinamine derivatives of J. Med. Chem. (1999), 42 (4), 730-741, nor any of the substituted N-[4-piperidinyl]-2-aminopyrimidines of Farmaco, Vol. 35, no. 11, 1980, pages 951-964.

This property renders the compounds according to the invention especially suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

A skilled person can make a selection of compounds based on the experimental data provided in the Experimental Part hereinafter. Any selection of compounds is embraced within this invention.

For example, the invention particularly relates to compounds of Formula (I), wherein $R^3$ is trifluoromethyl; and R, $R^4$ and $R^5$ are hydrogen.

Other interesting compounds of Formula (I) are those wherein $R^2$ is hydrogen or methyl.

Of particular interest are compounds of Formula (I) wherein $R^1$ is 4-fluorophenyl or 3,4-difluorophenyl.

Amongst the compounds of Formula (I), the most interesting are N-[1-(4-fluorobenzyl)piperidin-4-yl]-6-(trifluoromethyl)pyridazin-3-amine, and N-[1-(3,4-difluorobenzyl)piperidin-4-yl]-6-(trifluoromethyl)pyridazin-3-amine.

Throughout this application, the term "$C_{1-4}$alkyl" when used alone and when used in combinations such as "$C_{1-4}$alkyloxy", "perfluoro$C_{1-4}$alkyl", "di$C_{1-4}$alkylamino", includes, for example, methyl, ethyl, propyl, butyl, 1-methylpropyl, 1,1-dimethylethyl, the term; "$C_{1-6}$alkyl" includes methyl, ethyl, propyl, butyl, 1-methylpropyl, 1,1-dimethylethyl, pentyl and hexyl; "perfluoro$C_{1-4}$alkyl" includes for example trifluoromethyl, pentafluoro ethyl, heptafluoropropyl and nonafluorobutyl; $C_{3-8}$cycloalkyl includes cyclopropyl, cyclobutyl, cyclopentyl, cyclohexyl, cycloheptyl and cyclooctyl; $C_{5-7}$cycloalkenyl includes cyclopentenyl, cyclohexenyl and cycloheptenyl.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid. Conversely, said salts forms can be converted into the free forms by treatment with an appropriate base.

The term solvates refers to hydrates and alcoholates which the compounds of Formula (I) may form.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are embraced within the scope of this invention.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

In order to find antipsychotic compounds active against positive symptoms and having an improved safety profile (low EPS incidence and no metabolic disorders), we have screened for compounds selectively interacting with the dopamine D2 receptor and dissociating fast from this receptor. Compounds were first screened for their D2 affinity in a binding assay using [$^3$H]spiperone and human D2L receptor cell membranes. The compounds showing an $IC_{50}$ less than 1 μM were tested in an indirect assay adapted from a method published by Josee E. Leysen and Walter Gommeren, Journal of Receptor Research, 1984, 4(7), 817-845, to evaluate their rate of dissociation.

The compounds were further screened in a panel of more than 50 common G-protein coupled receptors (CEREP) and found to have a clean profile, that is to have low affinity for the tested receptors.

Some of the compounds have been further tested in in vivo models such as the "Apomorphine induced emesis test in Dogs" and the "Apomorphine test in rats" and found to be orally bio-available.

In view of the aforementioned pharmacology of the compounds of Formula (I), it follows that they are suitable for use as a medicine, in particular for use as an antipsychotic. More especially the compounds are suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

To optimize treatment of patients suffering from a disorder as mentioned in the foregoing paragraph, the compounds of Formula (I) may be administered together with other psychotropic compounds. Thus, in the case of schizophrenia, negative and cognitive symptoms may be targeted.

The present invention also provides a method of treating warm-blooded animals suffering from such disorders, said method comprising the systemic administration of a therapeutic amount of a compound of Formula (I) effective in treating the above described disorders.

The present invention also relates to the use of compounds of Formula (I) as defined hereinabove for the manufacture of a medicament, in particular an antipsychotic medicament, more especially a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to Formula (I).

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, an N-oxide form thereof and a prodrug thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Preparation

Compounds of formula (I),

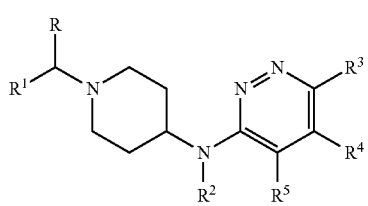

(I)

where R, $R^1$, $R^2$, $R^3$, $R^4$ and $R^5$ are as defined before, were prepared by reacting an intermediate of formula (II),

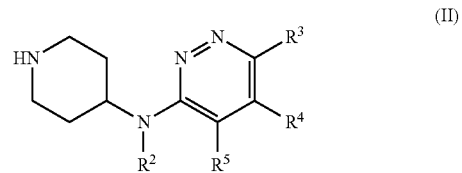

(II)

where $R^2$, $R^3$, $R^4$ and $R^5$ are as defined in formula (I), with an intermediate of formula $R_1$—C(=O)—R, where R and $R^1$ are as defined before, in the presence of a suitable reducing agent such as sodium triacetoxyborohydride, a suitable acid catalyst, such as acetic acid, in a suitable reaction inert solvent such as 1,2-dichloroethane.

Intermediates of formula (II), were prepared by reacting a protected piperidine derivative of formula (IV),

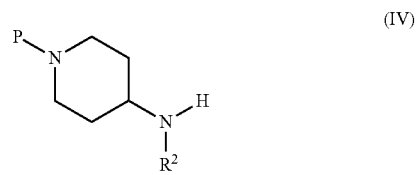

(IV)

where P represents a suitable protecting group, such as tert-butyloxycarbonyl, with a 3-chloropyridazine of formula (V),

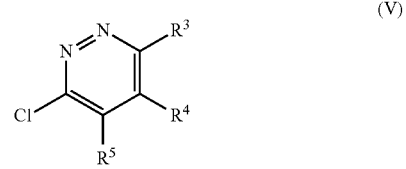

(V)

in the presence of a suitable catalyst, such as potassium iodide, under suitable reaction conditions, such as in a melt, followed by deprotection of the protecting group in intermediate (VI)

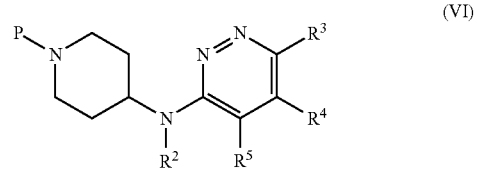

(VI)

under suitable condition, such as hydrochloric acid in methanol for the tert-butyloxycarbonyl group.

Intermediates of formula (V) are available either commercially or are prepared by procedures similar to those described in the chemical literature (for $R^3$=CF$_3$, see *Tetrahedron*, 1999, 55 (52), 15067-15070).

Compounds of formula (I) can also be prepared reacting a 3-chloropyridazine of formula (V) with a piperidine derivative of formula (VII)

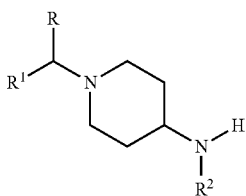

(VII)

in the presence of a suitable base such as diisopropylamine in a suitable solvent such as an alkanol, e.g. 1-butanol, at an elevated temperature.

Intermediates of formula (VII) were prepared by reacting 4,4-ethylenedioxypiperidine (VIII) with an intermediate of formula $R_1$—C(=O)—R, in the presence of a suitable reducing agent such as sodium triacetoxyborohydride, a suitable acid catalyst such as acetic acid, in a suitable reaction inert solvent such as 1,2-dichloroethane.

The resulting intermediate of formula (IX)

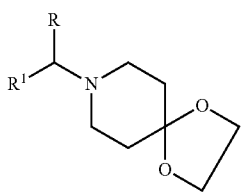

(IX)

was deprotected by treatment with an acid such as hydrochloric acid to give an intermediate of formula (X)

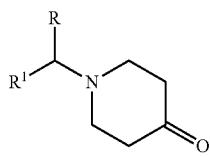

(X)

which was then reacted with an amine of formula $R^2$—$NH_2$ (XI), in the presence of a suitable reducing agent such as hydrogen, a suitable catalyst, such as palladium on carbon in a suitable reaction inert solvent such as ethanol.

The intermediates of formula (II) wherein $R^5$ represents chloro were prepared by reacting a piperidine of formula (XII)

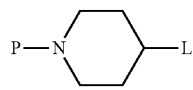

(XII)

wherein L represents a leaving group such as tosyl, with a pyridazine of formula (XIII)

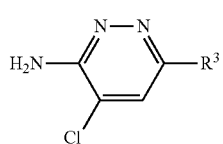

(XIII)

wherein $R^3$ is as defined before, in the presence of a suitable base such as sodium hydride in an aprotic solvent such as dimethylformamide, followed by deprotection of the protecting group in the intermediate of formula (VI) under suitable conditions, such as hydrochloric acid in methanol for the tert-butyloxycarbonyl group.

The intermediates of formula (XIII) can be prepared from pyridazines of formula (V) by amination and subsequent halogenation.

Experimental Part

Chemistry

Final purification of Examples (E1-E45) was carried out either by column chromatography on silica gel using the eluent described or by reversed phase preparative HPLC on a Hyperprep RP 18 BDS (Shandon) (8 μm, 200 mm, 250 g) column. Three mobile phases (mobile phase A: 90% 0.5% ammoniumacetate+10% acetonitrile; mobile phase B: methanol; mobile phase C: acetonitrile) were used to run a gradient method starting with 75% A and 25% B with a flow rate of 40 ml/min, hold for 0.5 minutes at the same conditions followed with an increase of the flow rate to 80 ml/min in 0.01 minutes to 50% B and 50% C in 41 minutes, to 100% C in 20 minutes and hold these conditions for 4 minutes.

$^1$H spectra were recorded on a Bruker DPX 360 spectrometer. The chemical shifts are expressed in ppm relative to tetramethylsilane.

Description 1 tert-Butyl 4-{-[6-(trifluoromethyl)pyridazin-3-yl]amino}piperidine-1-carboxylate (D1)

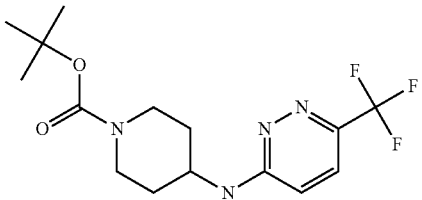

A mixture of 3-chloro-6-trifluoromethyl-pyridazine (4.4 g, 24.1 mmol) (prepared by a procedure similar to that described in *Tetrahedron*, 1999, 55 (52), 15067-15070), 4-amino-1-tert-butyloxycarbonylpiperidine (9.63 g, 48.1 mmol) and potassium iodide (cat.) were heated in a melt at 150° C. for 30 min. After this period, the reaction mixture was diluted with water and extracted with dichloromethane. The organic layer was separated, dried and the solvent evaporated in vacuo. The crude product was purified by chromatography (silica; 1%-4% ammonia in methanol (7 M)/dichloromethane) to give D1 (7.06 g, 85%). $C_{15}H_{21}F_3N_4O_2$ requires 346. Found 347 (MH$^+$)

Description 2

N-Piperidin-4-yl-6-(trifluormethyl)pyridazin-3-amine (D2)

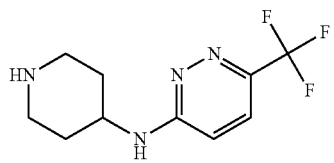 [SMILES: FC(F)(F)c1ccc(NC2CCNCC2)nn1]

A solution of D1 (7.06 g, 20.4 mmol) and hydrochloric acid/isopropanol (6N, 100 ml) in methanol (100 ml) was stirred at room temperature for 2 h. After this period, solvents were evaporated in vacuo and the residue triturated with acetonitrile. The solid product was filtered off and dried to give D2 as the di-hydrochloride salt (6.05 g, 95%). $C_{10}H_{13}F_3N_4$ requires 246. Found 247 (MH$^+$)

The di-hydrochloride salt (D2) was either used directly in the subsequent preparation of example compounds or alternatively converted to the free base prior to use. The free base was prepared by dissolution of the di-hydrochloric salt in water, basifying with sodium carbonate and extracting with dichloromethane. After drying (MgSO$_4$), the solvents were evaporated in vacuo to give the free base (D2a).

Description 3

8-(3,4-Difluorobenzyl)-1,4-dioxa-8-azaspiro[4.5]decane (D3)

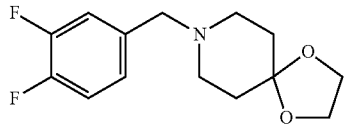 [SMILES: Fc1ccc(CN2CCC3(CC2)OCCO3)cc1F]

A solution of 3,4-difluorobenzaldehyde (4.40 g, 30.9 mmol), 4,4-ethylenedioxy-piperidine (4.40 g, 30.9 mmol), sodium triacetoxyborohydride (6.40 g, 30.2 mmol) and acetic acid (1.8 g, 30.0 mmol) in dichloroethane (200 ml) was stirred at room temperature for 18 h. After this period, the reaction mixture was washed with 1N sodium hydroxide. The organic layer separated, dried (MgSO$_4$) and the solvents evaporated in vacuo to give D3 (7.9 g, 98%). $C_{14}H_{17}F_2NO_2$ requires 269. Found 270 (MH$^+$)

Description 4

1-(3,4-Difluorobenzyl)piperidine-4-one (D4)

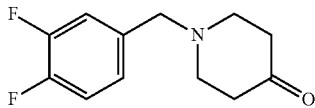

A solution of D3 (7.9 g, 29.4 mmol) in hydrochloric acid (5N, 150 ml) was heated at 50° C. for 2 h. After this period, the reaction mixture was washed with diisopropyl ether (100 ml) and then a saturated solution of sodium hydrogen carbonate (100 ml). The mixture was then extracted with dichloromethane and the extracts dried (MgSO$_4$) and the solvents evaporated in vacuo to give D4 (5.4 g, 82%). $C_{12}H_{13}F_2NO$ requires 225. Found 226 (MH$^+$)

Description 5

1-(3,4-Difluorobenzyl)-N-methylpiperidine-4-amine (D5)

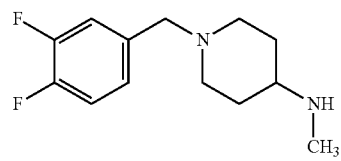 [SMILES: CNC1CCN(Cc2ccc(F)c(F)c2)CC1]

A suspension of D4 (5.4 g, 24 mmol), thiophene solution (4% in diisopropylether; 2 ml), methylamine solution (40% in water, 10 ml) and 10% palladium on carbon (2 g) in methanol (150 ml) were hydrogenated at atmospheric pressure and temperature until 1 eq. (~600 ml) of hydrogen had been taken up. After this period, the reaction mixture was filtered and the filtrate evaporated in vacuo. The crude product was purified by column chromatography (silica; 5%-10% ammonia in methanol/dichloromethane) to give D5 (4.7 g, 81%). $C_{13}H_{18}F_2N_2$ requires 240. Found 241 (MH$^+$)

Description 6

6-Trifluoromethyl-3-pyridazinamine (D6)

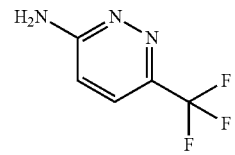 [SMILES: Nc1ccc(C(F)(F)F)nn1]

A mixture of 3-chloro-6-trifluoromethyl-pyridazine (1.6 g, 8.8 mmol) (prepared by a procedure similar to that described in Tetrahedron, 1999, 55 (52), 15067-15070) and ammonium hydroxide (30 ml) in THF (10 ml) was heated at 100° C. in a microwave reactor (Emrys Optimizer; 0-9 Barr) for 1 h. After this period, the reaction mixture was evaporated and the residue extracted with dichloromethane. The combined extracts were dried (MgSO$_4$), filtered and the solvents evaporated in vacuo to give D6 (1.3 g, 93%). $C_5H_4F_3N_3$ requires 163. Found 164 (MH$^+$)

Description 7

4-Chloro-6-trifluoromethyl-3-pyridazinamine (D7)

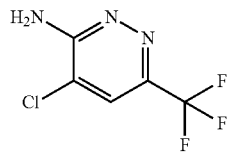 [SMILES: Nc1nnc(C(F)(F)F)cc1Cl]

A mixture of D6 (4.0 g, 24.5 mmol) and N-chlorosuccinimide (3.3 g, 24.5 mmol) in acetonitrile (160 ml) was heated at 70° C. for 18 h. After this period, the reaction was cooled to room temperature and the solvents evaporated in vacuo. The crude residue was purified by column chromatography (silica; 3%-5% methanol/dichloromethane) to give D7 (1.6 g, 33%). $C_5H_3ClF_3N_3$ requires 197. Found 198 (MH$^+$)

Description 8 tert-butyl 4-{[4-chloro-6-(trifluoromethyl)pyridazin-3-yl]amino}piperidine-1-carboxylate (D8)

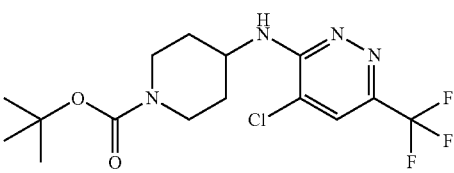 [SMILES: CC(C)(C)OC(=O)N1CCC(Nc2nnc(C(F)(F)F)cc2Cl)CC1]

To a stirred solution of D7 (1.6 g, 8.1 mmol) in dimethylformamide (50 ml) at 0° C., under nitrogen, was added NaH (60% in oil; 390 mg, 8.1 mmol) portionwise. The reaction mixture was stirred for 1 h., before 4-(toluene-4-sulfonyloxy)-piperidine-1-carboxylic acid tert-butyl ester (2.9 g, 8.1 mmol), dissolved in dimethylformamide (10 ml), was added dropwise. The reaction mixture was then heated between 80-90° C. for 6 hours. After cooling to room temperature, the solvents were evaporated in vacuo. The residue was dissolved in dichloromethane and washed with water. The organic layer was dried (MgSO$_4$), filtered and the solvents were evaporated in vacuo. The crude product was purified by column chromatography (silica gel; 3% methanol in dichloromethane) to give D8 (1.1 g, 37%). C$_{15}$H$_{20}$ClF$_3$N$_4$O$_2$ requires 380. Found 381 (MH$^+$).

Description 9

4-Chloro-N-piperidin-4-yl-6-(trifluoromethyl) pyridazin-3-amine (D9)

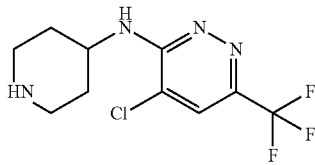 [SMILES: FC(F)(F)c1cc(Cl)c(NC2CCNCC2)nn1]

A solution of D8 (1.1 g, 2.9 mmol) and hydrochloric acid/isopropanol (6N, 20 ml) in methanol (100 ml) was stirred at room temperature for 18 h. After this period, the reaction mixture was evaporated in vacuo, the residue re-dissolved in methanol and the solution made alkaline with methanolic ammonia. The reaction mixture was concentrated in vacuo and the residue purified by column chromatography (silica gel; 5%-15% methanolic ammonia in dichloromethane) to give D9 (70 mg, 9%). C$_{10}$H$_{12}$ClF$_3$N$_4$ requires 280. Found 281 (MH$^+$).

Example 1

N-[1-(3,4-difluorobenzyl)piperidin-4-yl]-6-(trifluoromethyl)pyridazin-3-amine (E1)

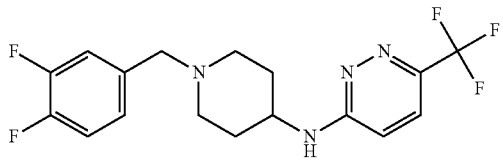 [SMILES: Fc1ccc(CN2CCC(Nc3ccc(C(F)(F)F)nn3)CC2)cc1F]

To a stirred solution of D2a (2.61 g, 10.6 mmol) and acetic acid (0.64 g, 10.6 mmol) in dichloroethane (200 ml) was added 3,4-difluorobenzaldehyde (1.52 g, 10.6 mmol) and sodium triacetoxyborohydride (2.24 g, 10.6 mmol) at room temperature. After stirring for 18 h., the reaction mixture was quenched with 1N sodium hydroxide, the organic layer removed, dried and the solvents evaporated in vacuo. The crude product was purified by chromatography (silica; 2%-5% ammonia in methanol (7 M)/dichloromethane) to give E1 (2.39 g, 61%). C$_{17}$H$_{17}$F$_5$N$_4$ requires 372. Found 373 (MH$^+$); mp: 167.7-168.9° C. $^1$H NMR (DMSO-D6) δ 1.50 (qd, J=11.5, 3.7 Hz, 1 H), 1.96 (br.d, J=12.4 Hz, 2 H), 2.12 (td, J=11.4, 2.6 Hz, 2 H), 2.78 (br.d, J=11.3 Hz, 2 H), 3.48 (s, 2 H), 3.90 (br.s, 1 H), 6.94 (d, J=9.4 Hz, 1 H), 7.13-7.19 (m, 1 H), 7.32-7.42 (m, 2 H), 7.53 (br.d, J=7.3 Hz, 1 H), 7.63 (d, J=9.4 Hz, 1 H)

Example 2

N-[1-(4-fluorobenzyl)piperidin-4-yl]-6-(trifluoromethyl)pyridazin-3-amine (E2)

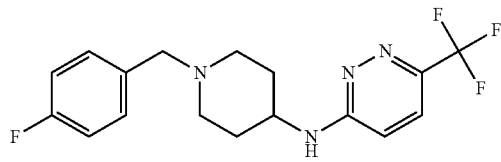 [SMILES: Fc1ccc(CN2CCC(Nc3ccc(C(F)(F)F)nn3)CC2)cc1]

A suspension of D2 (1.7 g, 5.32 mmol), 4-fluorobenzaldehyde (0.66 g, 5.32 mmol), diisopropylethylamine (1.37 g, 10.6 mmol) and triacetoxyborohydride on resin (Argonaut Technologies; 2.2 mmol/g; 3 eq.) in dichloroethane (10 ml) was stirred at room temperature for 18 h. After this period, the reaction mixture was filtered and the solvents evaporated in vacuo. The crude product was purified by chromatography (silica; 2%-6% ammonia in methanol (7 M)/dichloromethane) to give E2 (0.79 g, 42%). C$_{17}$H$_{18}$F$_4$N$_4$ requires 354. Found 355 (MH$^+$); mp: 163.3-165.3° C. $^1$H NMR (DMSO-D6) δ 1.48 (q, J=10.8 Hz, 2 H), 1.95 (br.d, J=12.5 Hz, 2 H), 2.09 (t, J=11.1 Hz, 2 H), 2.78 (br.d, J=11.3 Hz, 2 H), 3.47 (s, 2 H), 3.89 (br.s, 1 H), 6.94 (d, J=9.4 Hz, 1 H), 7.15 (t, J=8.8 Hz, 2 H), 7.34 (dd, J=8.3, 5.7 Hz, 2 H), 7.53 (br.d, J=7.3 Hz, 1 H), 7.63 (d, J=9.4 Hz, 1 H)

Example 12

N-[1-(3,4-difluorobenzyl)piperidin-4-yl]-N-methyl-6-(trifluoromethyl)pyridazine-3-amine (E12)

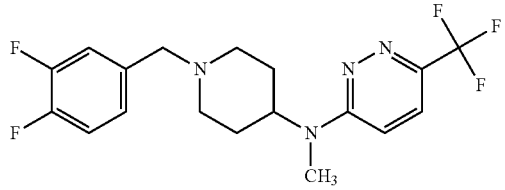 [SMILES: CN(c1ccc(C(F)(F)F)nn1)C1CCN(Cc2ccc(F)c(F)c2)CC1]

A solution of D5 (480 mg, 2 mmol), 3-chloro-6-trifluoromethylpyridazine (182 mg, 1 mmol) and diisopropylethylamine (260 mg, 2 mmol) in n-butanol (4 ml) was heated at 190° C. in a microwave reactor (Emrys Optimizer; 0-9 Barr) for 2 h. After this period, the reaction mixture was evaporated in vacuo and the residue extracted with dichloromethane. The organic layer was washed with a saturated solution of sodium hydrogen carbonate, dried (MgSO$_4$) and the solvents evaporated in vacuo. Purification by reverse phase HPLC (conditions as previously described) gave E12 (210 mg, 54%). C$_{18}$H$_{19}$F$_5$N$_4$ requires 386. Found 387 (MH$^+$). $^1$H NMR (CDCl$_3$) δ 1.74 (br.d, J=12.0 Hz, 2 H), 1.88 (qd, J=12.0, 3.9 Hz, 2 H), 2.17 (td, J=11.8, 2.5 Hz, 2 H), 2.96 (br.d, J=11.6 Hz, 2 H), 3.00 (s, 3 H), 3.47 (s, 2 H), 4.85 (t, J=12.1 Hz, 1 H), 6.78 (d, J=9.6 Hz, 1 H), 6.99-7.05 (m, 1 H), 7.10 (dt, J=10.2, 8.1 Hz, 1 H), 7.20 (ddd, J=11.4, 7.8, 2.1 Hz, 1 H), 7.46 (d, J=9.6 Hz, 1 H)

Example 16

N-[1-(4-chlorobenzyl)piperidin-4-yl]-6-chloro-pyridazin-3-amine (E16)

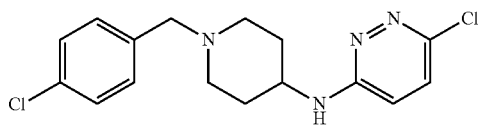 [SMILES: Clc1ccc(CN2CCC(Nc3ccc(Cl)nn3)CC2)cc1]

A solution of 1-(4-chlorobenzyl)-piperidin-4-yl amine (1 g, 4.45 mmol) (prepared by a procedure similar to that described in WO2001098273), 3,6-dichloropyridazine (670 mg, 4.45 mmol) and sodium carbonate (940 mg, 8.90 mmol) in dimethylacetamide (5 ml) was heated at 120° C. in a microwave reactor (Emrys Optimizer; 0-9 Barr) for 40 minutes. After this period, the reaction mixture was diluted with water and extracted with dichloromethane. The organic layer was dried (MgSO$_4$), filtered and the solvents evaporated in vacuo. Purification by reverse phase HPLC (conditions as previously described) gave E16 (228 mg, 15%). $C_{16}H_{18}Cl_2N_4$ requires 336. Found 337 (MH$^+$). $^1$H NMR (360 MHz, CDCl$_3$) δ1.52 (qd, J=11.5, 3.5 Hz, 2 H), 2.08 (d, J=12.5 Hz, 2 H), 2.16 (t, J=11.3 Hz, 2 H), 2.82 (d, J=11.5 Hz, 2 H), 3.48 (s, 2 H), 3.77-3.87 (m, 1 H), 4.55 (d, J=7.8 Hz, 1 H), 6.59 (d, J=9.3 Hz, 1 H), 7.14 (d, J=9.3 Hz, 1 H), 7.25 (d, J=7.7 Hz, 2 H), 7.29 (d, J=7.7 Hz, 2 H)

Example 45

(R,S)—N-[1-(3,4-difluoro-α-methylbenzyl)piperidin-4-yl]-6-(trifluoromethyl)pyridazin-3-amine (E45)

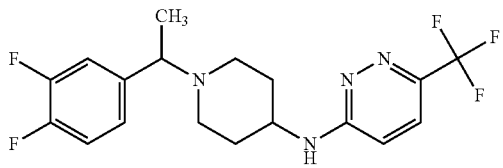 [SMILES: CC(c1ccc(F)c(F)c1)N1CCC(Nc2ccc(C(F)(F)F)nn2)CC1]

A solution of D2a (123 mg, 0.5 mmol), 3,4-difluoroacetophenone (186 mg, 1.25 mmol) and titanium isopropoxide (875 mg, 3 mmol) was stirred at room temperature for 1 h., before ethanol (0.7 ml) was added and the reaction stirred for a further 1 h. After this period, sodium cyanoborohydride (68 mg, 1.1 mmol) was added and the reaction stirred at room temperature overnight. The reaction mixture was then diluted with dichloroethane (30 ml), water (1 ml) was added and the mixture stirred and then filtered. The filtrate was evaporated in vacuo and the residue was re-dissolved in dichloromethane (30 ml), washed with 10% sodium carbonate solution and dried (MgSO$_4$). The mixture was filtered and the solvent evaporated in vacuo. Purification by reverse phase HPLC (conditions as previously described) gave E45 (106 mg, 55%). $C_{18}H_{20}F_4N_4$ requires 368. Found 369 (MH$^+$). $^1$H NMR (360 MHz, CDCl$_3$) δ 1.33 (d, J=6.7 Hz, 3 H), 1.45-1.62 (m, 2 H), 2.00-2.08 (m, 1 H), 2.09-2.21 (m, 3 H), 2.70-2.78 (m, 1 H), 2.90-3.00 (m, 1 H), 3.42 (q, J=6.7 Hz, 1 H), 3.85 (br.s, 1 H), 4.97 (d, J=7.3 Hz, 1 H), 6.65 (d, J=9.3 Hz, 1 H), 6.99-7.05 (m, 1 H), 7.09 (dt, J=10.1, 8.2 Hz, 1 H), 7.18 (ddd, J=11.7, 7.8, 2.1 Hz, 1 H), 7.42 (d, J=9.3 Hz, 1 H)

The following examples (E3-E11) were prepared from D2 or D2a and the corresponding benzaldehyde by a procedure similar to that described in Examples 1 and 2. Examples (E13-E14) were prepared from the corresponding benzaldehyde by a procedure similar to that described in Example 12.

| Example | R$^1$ | R$^2$ | M. Wt | MH+ |
|---|---|---|---|---|
| E1 | 3,4-difluorophenyl | H | 372 | 373 |
| E2 | 4-fluorophenyl | H | 354 | 355 |
| E3 | 4-chlorophenyl | H | 370 | 371 |
| E4 | 3-trifluoromethylphenyl | H | 404 | 405 |
| E5 | 3-fluorophenyl | H | 354 | 355 |
| E6 | 3,4,5-trifluorophenyl | H | 390 | 391 |

-continued

| Example | R¹ | R² | M. Wt | MH+ |
|---|---|---|---|---|
| E7 | cyclopentyl-CH₂ | H | 328 | 329 |
| E8 | 2-F-phenyl-CH₂ | H | 354 | 355 |
| E9 | 4-Cl-3-F-phenyl-CH₂ | H | 388 | 389 |
| E10 | 4-F-3-Cl-phenyl-CH₂ | H | 388 | 389 |
| E11 | 3,5-diF-phenyl-CH₂ | H | 372 | 373 |
| E12 | 3,4-diF-phenyl-CH₂ | CH₃ | 386 | 387 |
| E13 | 3-CF₃-phenyl-CH₂ | CH₃ | 418 | 419 |
| E14 | cyclopentyl-CH₂ | CH₃ | 342 | 343 |

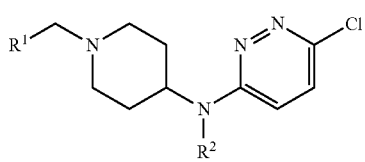

| Example | R¹ | R² | M. Wt | MH+ |
|---|---|---|---|---|
| E15 | phenyl-CH₂ | H | 302 | 303 |
| E16 | 4-Cl-phenyl-CH₂ | H | 336 | 337 |
| E17 | phenyl-CH₂ | CH₃ | 316 | 317 |
| E18 | 3,5-diF-phenyl-CH₂ | CH₃ | 352 | 353 |
| E19 | 2-CH₃-4-F-phenyl-CH₂ | CH₃ | 348 | 349 |
| E20 | 3,4-diF-phenyl-CH₂ | CH₃ | 352 | 353 |
| E21 | 3-Br-4-F-phenyl-CH₂ | CH₃ | 412 | 413 |
| E22 | 3-CF₃-4-Cl-phenyl-CH₂ | CH₃ | 418 | 419 |

The following Examples (E15-E38) were prepared by procedures similar to those described in Descriptions 1-5 and Examples 1, 2, 12 and 16.

-continued
| Example | R¹ | R² | M. Wt | MH+ |
|---|---|---|---|---|
| E23 | 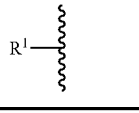 | CH₃ | 402 | 403 |
| E24 | 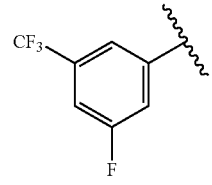 [SMILES: *c1cc(F)cc(C(F)(F)F)c1] | CH₃ | 402 | 403 |
| E25 | 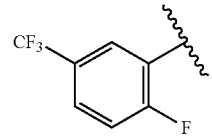 [SMILES: *c1cc(C(F)(F)F)ccc1F] | CH₃ | 384 | 385 |
| E26 | 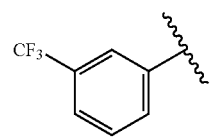 [SMILES: *c1cccc(C(F)(F)F)c1] | CH₃ | 344 | 345 |
| E27 | 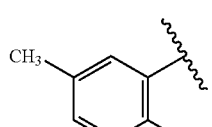 | CH₃ | 358 | 359 |
| E28 | 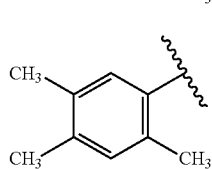 | CH₃ | 402 | 403 |
| E29 | 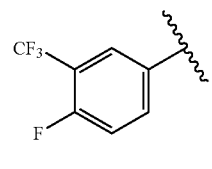 [SMILES: *c1ccc(F)c(C(F)(F)F)c1] | CH₃ | 348 | 349 |
| E30 | 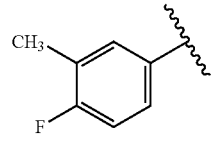 [SMILES: *c1ccc(F)c(C)c1] | CH₃ | 400 | 401 |
| E31 | 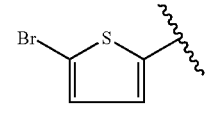 | CH₃ | 350 | 351 |
| E32 | 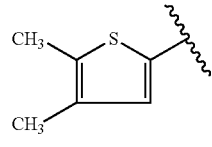 | CH₃ | 308 | 309 |
-continued
| Example | R¹ | R² | M. Wt | MH+ |
|---|---|---|---|---|
| E33 | 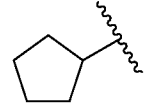 [SMILES: *C1CCCC1] | CH₃ | 320 | 321 |
| E34 | 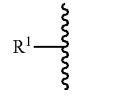 | CH₃ | 320 | 321 |
| E35 | 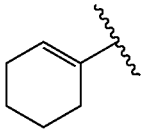 [SMILES: *C1=CCCCC1] | CH₃ | 370 | 371 |
| E36 | 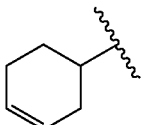 | CH₃ | 400 | 401 |
| E37 | 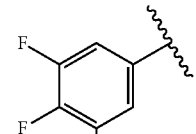 | CH₃ | 348 | 349 |
| E38 | 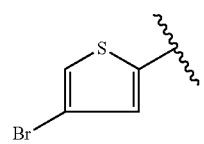 [SMILES: *c1cc(Br)cs1] | CH₃ | 359 | 360 |
| E39 | 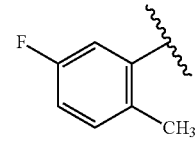 | CH₃ | 336 | 337 |
The following Example (E40) was prepared by procedures similar to those described in Descriptions 1-5 and Examples 1, 2 and 12.
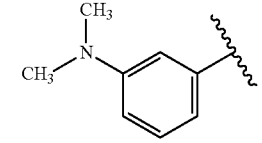 [SMILES: *c1cccc(N(C)C)c1]

| Example | R¹ (with R² shown above) | R² | M. Wt | MH+ |
|---|---|---|---|---|
| E40 | 3-(trifluoromethyl)phenyl | CH₃ | 364 | 365 |

The following Examples (E41-E45) were prepared by procedures similar to those described in Descriptions 1-9 and Examples 1, 2, 12, 16 and 45.

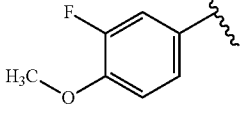

| Example | R¹ | R | R⁵ | M. Wt | MH+ |
|---|---|---|---|---|---|
| E41 | 3-fluoro-4-methoxyphenyl | H | H | 384 | 385 |
| E42 | 2,4-difluorophenyl | H | H | 372 | 373 |
| E43 | 3,4-difluorophenyl | H | Cl | 406 | 407 |
| E44 | 4-fluorophenyl | CH₃ | H | 368 | 369 |
| E45 | 3,4-difluorophenyl | CH₃ | H | 386 | 287 |

The following names refer to the Example Numbers:
N-[1-(3,4-difluorobenzyl)piperidin-4-yl]-6-(trifluoromethyl)pyridazin-3-amine (E1)
N-[1-(4-fluorobenzyl)piperidin-4-yl]-6-(trifluoromethyl)pyridazin-3-amine (E2)
N-[1-(4-chlorobenzyl)piperidin-4-yl]-6-(trifluoromethyl)pyridazin-3-amine (E3)
N-[1-(3-trifluormethylbenzyl)piperidin-4-yl]-6-(trifluoromethyl)pyridazin-3-amine (E4)
N-[1-(3-fluorobenzyl)piperidin-4-yl]-6-(trifluoromethyl)pyridazin-3-amine (E5)
N-[1-(3,4,5-trifluorobenzyl)piperidin-4-yl]-6-(trifluoromethyl)pyridazin-3-amine (E6)
N-[1-(cyclopentylmethyl)piperidin-4-yl]-6-(trifluoromethyl)pyridazin-3-amine (E7)
N-[1-(2-fluorobenzyl)piperidin-4-yl]-6-(trifluoromethyl)pyridazin-3-amine (E8)
N-[1-(4-chloro-3-fluorobenzyl)piperidin-4-yl]-6-(trifluoromethyl)pyridazin-3-amine (E9)
N-[1-(3-chloro-4-fluorobenzyl)piperidin-4-yl]-6-(trifluoromethyl)pyridazin-3-amine (E10)
N-[1-(3,5-difluorobenzyl)piperidin-4-yl]-6-(trifluoromethyl)pyridazin-3-amine (E11)
N-[1-(3,4-difluorobenzyl)piperidin-4-yl]-N-methyl-6-(trifluoromethyl)pyridazin-3-amine (E12)
N-[1-(3-trifluoromethylbenzyl)piperidin-4-yl]-N-methyl-6-(trifluoromethyl)pyridazin-3-amine (E13)
N-[1-(cyclopentylmethyl)piperidin-4-yl]-N-methyl-6-(trifluoromethyl)pyridazin-3-amine (E14)
N-[1-(4-chlorobenzyl)piperidin-4-yl]-6-chloropyridazin-3-amine (E16)
N-(1-benzylpiperidin-4-yl)-N-methyl-6-chloropyridazin-3-amine (E17)
N-[1-(3,5-difluorobenzyl)piperidin-4-yl]-N-methyl-6-chloropyridazin-3-amine (E18)
N-[1-(2-fluoro-5-methylbenzyl)piperidin-4-yl]-N-methyl-6-chloropyridazin-3-amine (E19)
N-[1-(3,4-difluorobenzyl)piperidin-4-yl]-N-methyl-6-chloropyridazin-3-amine (E20)
N-[1-(3-bromo-4-fluorobenzyl)piperidin-4-yl]-N-methyl-6-chloropyridazin-3-amine (E21)
N-[1-(4-chloro-3-trifluoromethylbenzyl)piperidin-4-yl]-N-methyl-6-chloropyridazin-3-amine (E22)
N-[1-(3-fluoro-5-trifluoromethylbenzyl)piperidin-4-yl]-N-methyl-6-chloropyridazin-3-amine (E23)
N-[1-(2-fluoro-5-trifluoromethylbenzyl)piperidin-4-yl]-N-methyl-6-chloropyridazin-3-amine (E24)
N-[1-(3-trifluoromethylbenzyl)piperidin-4-yl]-N-methyl-6-chloropyridazin-3-amine (E25)
N-[1-(2,5-dimethylbenzyl)piperidin-4-yl]-N-methyl-6-chloropyridazin-3-amine (E26)
N-[1-(2,4,5-trimethylbenzyl)piperidin-4-yl]-N-methyl-6-chloropyridazin-3-amine (E27)
N-[1-(4-fluoro-3-trifluoromethylbenzyl)piperidin-4-yl]-N-methyl-6-chloropyridazin-3-amine (E28)
N-[1-(4-fluoro-3-methylbenzyl)piperidin-4-yl]-N-methyl-6-chloropyridazin-3-amine (E29)
N-[1-(5-bromothiophen-2-ylmethyl)piperidin-4-yl]-N-methyl-6-chloropyridazin-3-amine (E30)
N-[1-(4,5-dimethylthiophen-2-ylmethyl)piperidin-4-yl]-N-methyl-6-chloropyridazin-3-amine (E31)
N-[1-(cyclopentylmethyl)piperidin-4-yl]-N-methyl-6-chloropyridazin-3-amine (E32)
N-[1-(1-cyclohex-1-en-ylmethyl)piperidin-4-yl]-N-methyl-6-chloropyridazin-3-amine (E33)
N-[1-(1-cyclohex-3-en-ylmethyl)piperidin-4-yl]-N-methyl-6-chloropyridazin-3-amine (E34)
N-[1-(3,4,5-trifluorobenzyl)piperidin-4-yl]-N-methyl-6-chloropyridazin-3-amine (E35)
N-[1-(4-bromothiophen-2-ylmethyl)piperidin-4-yl]-N-methyl-6-chloropyridazin-3-amine (E36)

N-[1-(3-fluoro-6-methylbenzyl)piperidin-4-yl]-N-methyl-6-chloropyridazin-3-amine (E37)
N-[1-(3-dimethlyamino-benzyl)piperidin-4-yl]-N-methyl-6-chloropyridazin-3-amine (E38)
N-[1-(3-trifluoromethylbenzyl)piperidin-4-yl]-N-methyl-6-methylpyridazin-3-amine (E40)
N-[1-(3-fluoro-4-methoxybenzyl)piperidin-4-yl]-6-(trifluoromethyl)pyridazin-3-amine (E41)
N-[1-(2,4-difluorobenzyl)piperidin-4-yl]-6-(trifluoromethyl)pyridazin-3-amine (E42)
N-[1-(3,4-difluorobenzyl)piperidin-4-yl]-6-(trifluoromethyl)-4-chloro-pyridazin-3-amine (E43)
N-[1-(4-fluoro-α-methylbenzyl)piperidin-4-yl]-6-(trifluoromethyl)pyridazin-3-amine (E44)
N-[1-(3,4-difluoro-α-methylbenzyl)piperidin-4-yl]-6-(trifluoromethyl)pyridazin-3-amine (E45)

Pharmacology

In vitro Binding Affinity for Human $D2_L$ Receptor

Frozen membranes of human Dopamine $D2_L$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand [$^3$H] Spiperone (NEN, specific activity ~70 Ci/mmol) was diluted in assay buffer at a concentration of 2 nmol/L. Prepared radioligand (50 μl), along with 50 μl of either the 10% DMSO control, Butaclamol ($10^{-6}$ mol/l final concentration), or compound of interest, was then incubated (30 min, 37° C.) with 400 μl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful). All compounds had a $pIC_{50}$ values>6.0 except E8, E25, E41, E42, E44 and E45 ($pIC_{50}$>5.2).

Fast Dissociation

Compounds showing an $IC_{50}$ superior to 1 μM were tested in an indirect assay adapted from a method published by Josee E. Leysen and Walter Gommeren, Journal of Receptor Research, 1984, 4(7), 817-845, to evaluate their rate of dissociation. Compounds at a concentration of 4 times their $IC_{50}$ were first incubated for one hour with human D2L receptor cell membranes in a volume of 2 ml at 25° C., then filtered over glass-fibre filter under suction using a 40 well multividor. Immediately after, the vacuum was released. 0.4 ml of pre-warmed buffer (25° C.) containing 1 nM [$^3$H] spiperone was added on the filter for 5 minutes. The incubation was stopped by initiating the vacuum and immediate rinsing with 2×5 ml of ice-cold buffer. The filter-bound radioactivity was measured in a liquid scintillation spectrometer. The principle of the assay is based on the assumption that the faster a compound dissociates from the D2 receptor, the faster [$^3$H]spiperone binds to the D2 receptor. For example, when D2 receptors are incubated with clozapine at the concentration of 1850 nM (4×$IC_{50}$), [$^3$H]spiperone binding is equivalent to 60-70% of its total binding capacity (measured in absence of drug) after 5 min incubation on filter. When incubated with other antipsychotics, [$^3$H]spiperone binding varies between 20 and 50%. Since clozapine was included in each filtration run, tested compounds were considered fast dissociating D2 antagonists if they were dissociating as fast or faster than clozapine. All measured compounds had a dissociation rate faster than that of clozapine, i.e. >50%.

The invention claimed is:

1. A method of treating a patient with psychosis selected from the group consisting of schizophrenia, schizophreniform disorder, schizoaffective disorder comprising administering to said patient a therapeutically effective amount to treat psychosis of a compound of formula (I)

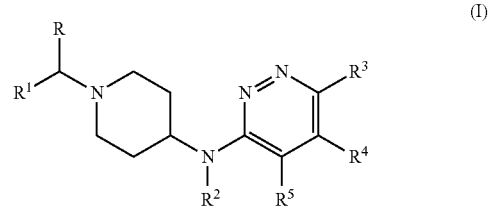

or a pharmaceutically acceptable salt, hydrate or solvate thereof, or a stereoisomeric form thereof, wherein
R is hydrogen or $C_{1-6}$alkyl;
$R^1$ is phenyl; phenyl substituted with 1, 2 or 3 substituents each independently selected from the group consisting of hydrogen, halo, cyano, $C_{1-4}$alkyl, $C_{1-4}$alkyloxy, perfluoro$C_{1-4}$alkyl, di$C_{1-4}$alkylamino; thienyl; thienyl substituted with 1 or 2 substituents selected from the group consisting of halo and $C_{1-4}$alkyl; $C_{3-8}$cycloalkyl; or $C_{5-7}$cycloalkenyl;
$R^2$ is hydrogen or $C_{1-6}$alkyl;
$R^3$ is halo, $C_{1-4}$alkyl or perfluoro$C_{1-4}$alkyl; and
$R^4$ and $R^5$ each independently are hydrogen or halo.

2. The method of claim 1 wherein the psychosis is schizophrenia.

* * * * *